United States Patent
Wahl

(10) Patent No.: US 8,067,194 B2
(45) Date of Patent: Nov. 29, 2011

(54) HYDROLYSIS PROCESS FOR RAW MATERIALS FROM THE FISHING AND SLAUGHTERHOUSE INDUSTRIES AND TANKS FOR USE THEREIN

(75) Inventor: Tony Wahl, Vigra (NO)

(73) Assignee: Wahl Process Systems AS, Vigra (NO)

( * ) Notice: Subject to any disclaimer, the term of this patent is extended or adjusted under 35 U.S.C. 154(b) by 1115 days.

(21) Appl. No.: 11/817,365

(22) PCT Filed: Mar. 3, 2006

(86) PCT No.: PCT/NO2006/000080
§ 371 (c)(1),
(2), (4) Date: Sep. 9, 2007

(87) PCT Pub. No.: WO2006/096067
PCT Pub. Date: Sep. 14, 2006

(65) Prior Publication Data
US 2009/0123965 A1    May 14, 2009

(30) Foreign Application Priority Data
Mar. 8, 2005  (NO) .................................... 20051216

(51) Int. Cl.
*C12P 1/00* (2006.01)
*C12M 1/00* (2006.01)

(52) U.S. Cl. ........ 435/41; 435/289.1; 435/183; 435/195; 422/224; 422/232; 422/129; 422/187; 422/608; 422/646; 210/767; 210/744

(58) Field of Classification Search ................ 435/68.1, 435/41, 183, 195, 289.1; 422/224, 232, 129, 422/187, 608, 646; 210/767, 744
See application file for complete search history.

(56) References Cited

U.S. PATENT DOCUMENTS

| | | | | |
|---|---|---|---|---|
| 4,378,162 A * | 3/1983 | Bracegirdle | ...................... | 366/7 |
| 5,806,205 A * | 9/1998 | Varvat | .............................. | 34/181 |
| 6,030,112 A * | 2/2000 | Milek | ............................. | 366/64 |
| 6,210,436 B1 * | 4/2001 | Weadock | ....................... | 623/1.39 |
| 6,465,236 B1 * | 10/2002 | Nishino et al. | ................ | 435/221 |
| 6,995,242 B2 | 2/2006 | Nnanna et al. | | |
| 2002/0122780 A1 * | 9/2002 | McManus et al. | ........... | 424/70.6 |

FOREIGN PATENT DOCUMENTS
EP          1488901 A1 * 12/2004
WO     2004071202 A1    8/2004

* cited by examiner

*Primary Examiner* — Susan Hanley
(74) *Attorney, Agent, or Firm* — Dennison, Schultz & MacDonald

(57) ABSTRACT

The invention relates to a method and hydrolysis tank for enzymatic hydrolysis of raw materials containing collagen and proteins to produce the three layers: a top layer containing fat, a mid-layer comprising water soluble constituents and denatured collagen, and a non-soluble bottom layer comprising bones and non-soluble proteins. These layers are separated and the second layer is further separated by cooling for a time period sufficient to form two layers: a bottom layer containing partially or wholly set collagen, and a liquid top layer containing the remaining water soluble proteins which are removed. The other is heated until it becomes liquid. The hydrolysis tank comprises a turnable stirring mechanism, a device for heat exchange and a reversible screw that is arranged in the bottom of the tank. A clearing sump for separation of collagen, includes an inlet for supply of hydrolysate.

16 Claims, 5 Drawing Sheets

HYDROLYSIS PROCESS FOR RAW MATERIALS FROM THE FISHING AND SLAUGHTERHOUSE INDUSTRIES AND TANKS FOR USE THEREIN

This application is a national stage entry of PCT/NO06/00080, filed Mar. 3, 2006, which claims priority to Norwegian Application No. 20051216, filed Mar. 8, 2005.

BACKGROUND OF THE INVENTION

The present invention relates to a method for an enzymatic hydrolysis process of collagen and raw materials containing proteins, comprising the following steps:
(1) the raw materials undergo enzymatic hydrolysis to produce the three following layers:
  (a) a top layer containing fat,
  (b) a mid layer comprising water soluble constituents, among others water soluble proteins, including collagen, and
  (c) a non-soluble bottom layer comprising bones and non-soluble proteins; and
(2) (a), (b) and (c) are separated; and
(3) (b) is further separated.

The invention also relates to an hydrolysis tank comprising an inlet for supply of raw materials and an outlet for products, a turnable stirring mechanism, and a device for heat exchange; and a clearing sump for separation of collagen, including an inlet for supply of hydrolyzat, and an outlet for collagen and the remaining components, and applications thereof in an hydrolysis process of collagen and raw materials containing proteins.

The production of food, for example within the fishing industry and slaugtherhouse industry, produces large amounts of by-products, very rich in valuable components, including proteins, oils and calcium. In order to recover to these resources, several processes for releasing these valuable components have been developed. These processes are often based on ensilage or enzymatic hydrolysis. This, however, produces proteins and oils of a quality that does not meet the requirements of the food industry. They can therefore only be used for the production of fodder.

For the making of products that meet the requirements of the food industry, enzymes that are able to split the raw material into its separate constituents have been developed. These enzymes provide for an enzymatic hydrolysis of for example slaugtherhouse waste. The proteins in the raw material are then resolved in water, so that the protein, oil and bone parts can be separated. These enzymes are commercially available.

Within the fishing industry, large amounts of by-products are produced, with high contents of valuable proteins and oils. There is currently some activity in the industry to recover these, based on ensilage. Enzymatic hydrolysis has also been tried.

SUMMARY OF THE INVENTION

The invention relates to a method for running the hydrolysis process non-continuously. Continuous hydrolysis processes already exist; they have, however, several drawbacks. Because they are continuous processes, there is some unrestrained flow between tanks and process steps. This leads to uneven hydrolysis of the raw material. The finished hydrolyzat product contains collagen, making it a mixed product of limited usability. Hydrolyzat made from such processes is not suitable as food for humans.

The inventor of the present invention has developed a "batch" process to run an enzymatic hydrolysis on raw materials from the fishing and slaugtherhouse industries. The product from this process will also be suitable as food for humans.

The hydrolysis process according to the present invention takes place using enzymes that are commercially available, but in a tank newly developed by the inventor. The hydrolysis tank is provided with an extraordinary high mixing capacity, in that large screws in the bottom of the tank will push the contents thereof towards the center of the tank, allowing the stirring mechanism to be applied most effectively. Thorough mixing, together with a large heating surface, make it possible to keep the temperature very stable, optimizing the hydrolysis process. Being a closed "batch" system, as opposed to the continuous process systems currently in use, not only achieves an accurate regulation of temperature, but also an equally accurate regulation of the time intervals for the hydrolyzat to remain under different temperatures.

The hydrolysis process results in three parts, one of them including proteins; collagen, among others. The inventor has developed a new method for effective separation of the collagen from the other proteins. The method comprises a quick cooling of the water soluble proteins without resorting to agitation. The collagen, being denaturated and thereby liquid at high temperatures, will precipitate at the bottom of the sump in a natural, solid state. The remaining water soluble proteins may then be pumped out, whereafter the collagen is heated to a denaturated, liquid state so that it also can be removed from the clearing sump.

To be able to accomplish an effective separation of collagen from the other water soluble proteins in the hydrolyzat, the inventor has developed a new type of clearing sump. This sump is able to perform cooling and heating of fluids, in this case hydrolyzat, very quickly and homogeneously. Since cooling must be achieved without resorting to agitation, stirring can not be applied to get an even distribution of temperature. The sump therefore contains large cooling/heating surfaces, so that the cooling/heating surface area by volume of fluid ratio will be very large, and the fluid will be cooled/heated fast and homogeneously.

The method according to the invention is thus characterized by cooling without agitation, of a midlayer (b) containing water soluble constituents, including water soluble proteins of which collagen is one, until it reaches a temperature, and under a time period sufficient for the forming of two layers;
(d) a bottom layer containing partially or wholly set collagen, and
(e) a liquid top layer containing the remaining water soluble proteins; removal of (e); and heating of (d) until it becomes liquid.

The hydrolysis tank according to the invention is characterized by the provision of one or several reversable screws at outlets at the bottom of the tank.

The clearing sump according to the invention is characterized in that it comprises a heat exchange system including heating jackets surrounding the tank as well as vertical heating/cooling surfaces in the interior of the tank, which surfaces may have wave form to increase the surface area.

BRIEF DESCRIPTION OF THE DRAWINGS

The invention will now be described in more detail with reference to the accompanying drawings, where.

DESCRIPTION OF THE PREFERRED EMBODIMENTS

Figure 1:
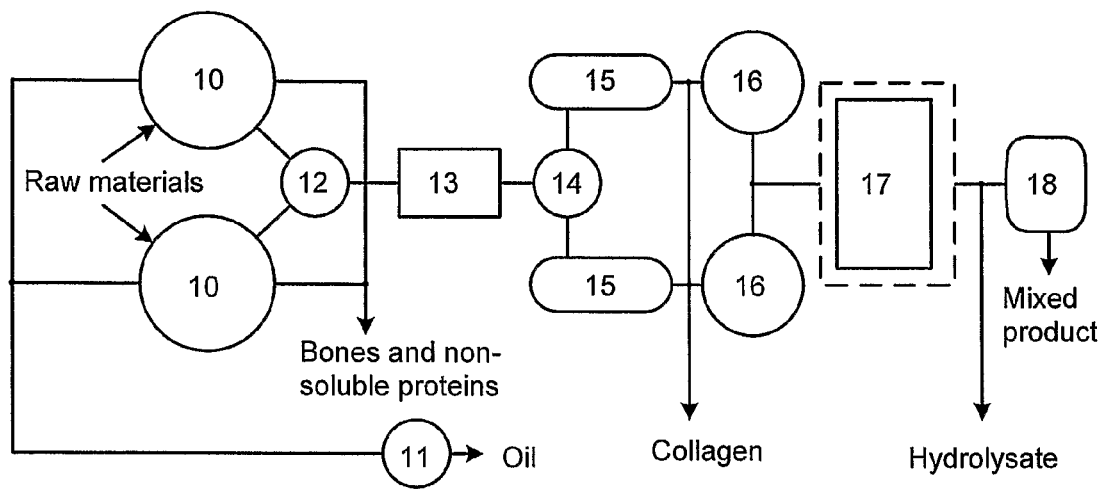
FIG. 1 shows a flow chart for an enzymatic hydrolysis process according to a preferred embodiment of the invention.

The hydrolysis process may be described in more detail with reference to FIG. 1. The arrows in FIG. 1 indicates where raw materials are supplied and where products exit. An hydrolysis tank 10 is filled with raw materials in the form of by-products from the fishing industry or the slaugtherhouse industry. Raw materials from the fishing industry may be whole fish or parts thereof like for example heads, bones, skin or guts. Raw materials from the fishing industry also include shellfish. Corresponding raw materials from the slaugtherhouse industry may also be used, including all parts of an animal, or the entire animal. The expression "animal" is here meant to include birds, like for example poultry. The process according to the invention may be adopted to all kinds of raw materials containing proteins and collagen, that is, bones, connective tissue, and skin/hide. The raw material will typically consist of a mixture of several by-products from the processing industries, but it may of course consist of only one type of raw material.

Hot water is added to the raw material in the hydrolysis tank(s) 10. The temperature is regulated so that it will be optimal for the enzymatic hydrolysis. It will thus vary according to the particular enzymes being used. When the desired temperature is reached, the enzymes are added, starting the hydrolysis process. The enzymes will catalyse the hydrolysis, resulting in large amounts of proteins contained in the raw material being resolved in the water. Besides the water soluble proteins, oils, bones and non-soluble proteins are also released.

When the raw material is sufficiently hydrolysed, the enzymes will typically be deactivated by an increase in the temperature. The mixture is then rested. After a short period of time, clearly separated layers are formed. On top an oil layer is formed, then a water soluble layer containing the resolved proteins, and at the bottom of the tank the heaviest layer is found, consisting of non-soluble proteins and bones. For the remaining part of this description, these layers will be referred to as the oil layer, the hydrolyzat and the bone layer, respectively.

The hydrolysis process will normally go on for a total of 3-4 hours, depending on how fast raw materials are added and products removed. First, the oil is removed from the hydrolysis tank, normally by draining, after which it may be separated in an oil separator 11. The hydrolyzat is then drained out from the hydrolysis tank while the bone layer remains in the tank. The bone layer is finally removed from the bottom of the hydrolysis tank.

Being removed from the hydrolysis tank, the hydrolyzat is filtered through a conventional filter 12. The last remains of oil and bone are then removed from the hydrolyzat in a cascade tank 13 and by a subsequent separation in a separator 14.

From the separator the hydrolyzat will be directed to a clearing sump 15. In this sump, the temperature is reduced without agitation, so that the collagen will set as gelatine, i.e. in a coagulated form. The temperature sufficiently low to make the collagen set, will vary depending on the type of raw material being used, and often reflects the body temperature of the original fish/animal/bird. Collagen from fish will thus set at a lower temperature than those from animals. Typically, for the collagen to set, the hydrolyzat will have to be cooled to a temperature in the range of 10-25° C., preferably 20-22° C., for fish; 25-40° C., preferably 32-35° C., for animals and 30-45° C., preferably 33-40° C. for birds. The collagen has a higher density than the remaining hydrolyzat, and it will therefore sink. Two distinctly separated layers will thus form in the sump. At the bottom, solid state collagen will set and on top of this, the remaining, liquid state hydrolyzat. The collagen will set, totally or partially, because of the reduced temperature.

After draining of the liquid state hydrolyzat to a buffer tank 16 the temperature in the sump is raised, so that the collagen also will become liquid and thus can be removed from the sump, typically by pumping or draining. The amount of increase in temperature depends on what the collagen will be used for. If it is to be conserved further, it will be removed as soon as it becomes liquid. This will be done at a temperature that will vary, depending on the type of raw materials used for producing the collagen, typically, this temperature will be about 10-25° C. higher than the separating temperature for the collagen. If the collagen is not to be conserved, but used for other purposes, it must be heated to at least 65° C. before it is removed, to avoid microbial flourishing.

The hydrolyzat, with the collagen removed, may now undergo further treatment by methods known from other areas. The hydrolyzat is preferably treated in a evaporator 17, so that the content of dry mass will increase to the desired level. With the collagen removed, the dry mass level will be around 3-15%, typically about 7%. The amount of evaporation depends on what the hydrolyzat will be used for. If, for example, a hydrolyzat from fish is to be transferred back to the fish, by injection into the meat, it must have precisely the same amount of dry mass as the meat, this being around 15%. If the hydrolyzat is evaporated to around 60%, it will become self conserving, which of course will be advantageous for long-term storage. The costs, however, will increase with the level of evaporation, and this will normally limit the level of evaporation of the hydrolyzat. It is essential for the evaporation process, that the collagen is separated from the hydrolyzat. Hydrolyzat with collagen not removed, has a viscosity that is too high, meaning that the evaporator will not work. By removing the collagen, as in the method according to the invention, the protein bearing hydrolyzat may be further treated to achieve a dry mass content that will give a better storage quality and usefulness in many areas, including food for humans as well as animals.

The hydrolyzat may of course be used immediately after evaporation, and in this case it will be transferred to a product mixer 18 for mixing with other constituents. The collagen may now be transferred back to the hydrolyzat if desired. Since a large amount of water has been removed in the evaporator, one would not in this way get a product corresponding to an instance where the collagen was not removed from the hydrolyzat in the first place. The product will thus be of a higher concentration, and more suitable for storage and shipping. Of course the collagen need not be transferred back to the hydrolyzat. After removal from the sump, it may be kept separately and used for other purposes.

FIG. 1 illustrates a process where two hydrolysis tanks, two clearing sumps and two buffer tanks are used. This is a preferred embodiment of the invention, but one could just as well use only one, or several of these tanks. The tanks represent places where the process fluid will remain for a period of time, so it might be advantageous, but not necessary, to use several tanks of different types, to maximize the capacity of the hydrolysis plant.

The Hydrolysis Tank

To be able to achieve a hydrolysis process that will be as complete as possible, and in the shortest possible time span, the design of the hydrolysis tank will be essential. One must be able to heat the contents of the tank evenly and effectively, and thus agitation will be important. This is achieved through stirring to keep the temperature through-out the tank at an even level. Stirring is done more effectively in that a screw at the bottom of the tank pushes larger bones etc., that are likely to gather at the bottom, towards the center of the tank, where they are brought in contact with the stirring mechanism. In addition to creating a homogeneous distribution of temperature, stirring also contributes in giving the enzymes physical access to all of the raw material. In order to achieve this, the inventor has designed a new type of hydrolysis tank, illustrated in more detail in FIGS. 2-6.

The hydrolysis tank may of course vary in size, according to specific needs. In the embodiment of the invention described here, the tank has a capacity of 25.000 liters. This tank is of a size that makes it suitable for construction centrally, and subsequent transportation on narrow roads. Smaller tanks could, however, be designed for small aquaculture plants, larger tanks for other means of transportation, or very large tanks for construction on site, and the dimensions may of course be adjusted.

At the bottom of the hydrolysis tank 10 there are one or several outlets 20 for removal of the bone layer. The outlets 20 are preferably positioned in recesses in the bottom wall of the tank, and with an angle to the horizontal. This angle may be in the range of 5-45°, preferably 15-30°, more preferably 20°. Gravity will thus contribute when remains of bone are lead through the outlets, while the angle remains small enough for the screws 21 in the outlets to be able to push the raw materials towards the center of the tank, during heating and mixing of raw materials, enzymes and water. The outlets contain screws 21 that can be turned both ways. Valves 22 are provided for at the ends of the outlets. The outlets are also surrounded by heating jackets 23. The size of the outlets may of course vary. They must be large enough to be able to transport remains of bone of varying sizes, depending on the type of raw material being used. In the preferred embodiment of FIGS. 2-5, an outlet having a diameter of 200 mm is used.

The hydrolysis tank has one or more inlets for steam 24, and one or more outlets for steam and condensate 25. Side walls 26, bottom 27 and internal cylinder 28 are all provided with heating jackets 29. There is thus a large area of contact between process steam and the contents of the tank, this area comprising the tank's bottom 27, side walls 26, internal cylinder 28 and ceiling 30.

The hydrolysis tank may be mounted on different types of bases, a preferred type being 6 legs 31 with adjustable height.

Temperature and level transmitters 32 are mounted to provide for control during the hydrolysis process. A step 33 is mounted to provide for easy access to the top of the hydrolysis tank.

A lid 34 is mounted on top 30 of the tank to provide for access to the interior of the tank. The top 30 is also provided with an inlet 35 for the adding of raw materials, water and enzymes. A valve with a cap 36 is also mounted on top of the tank, to provide for ventilation of the tank. Above and across the tank a beam 37 is arranged, on which a motor 38 is mounted for driving the stirring mechanism. The beam 37 provides for both structural support, and the possibility of the installation of piping.

Figure 5:
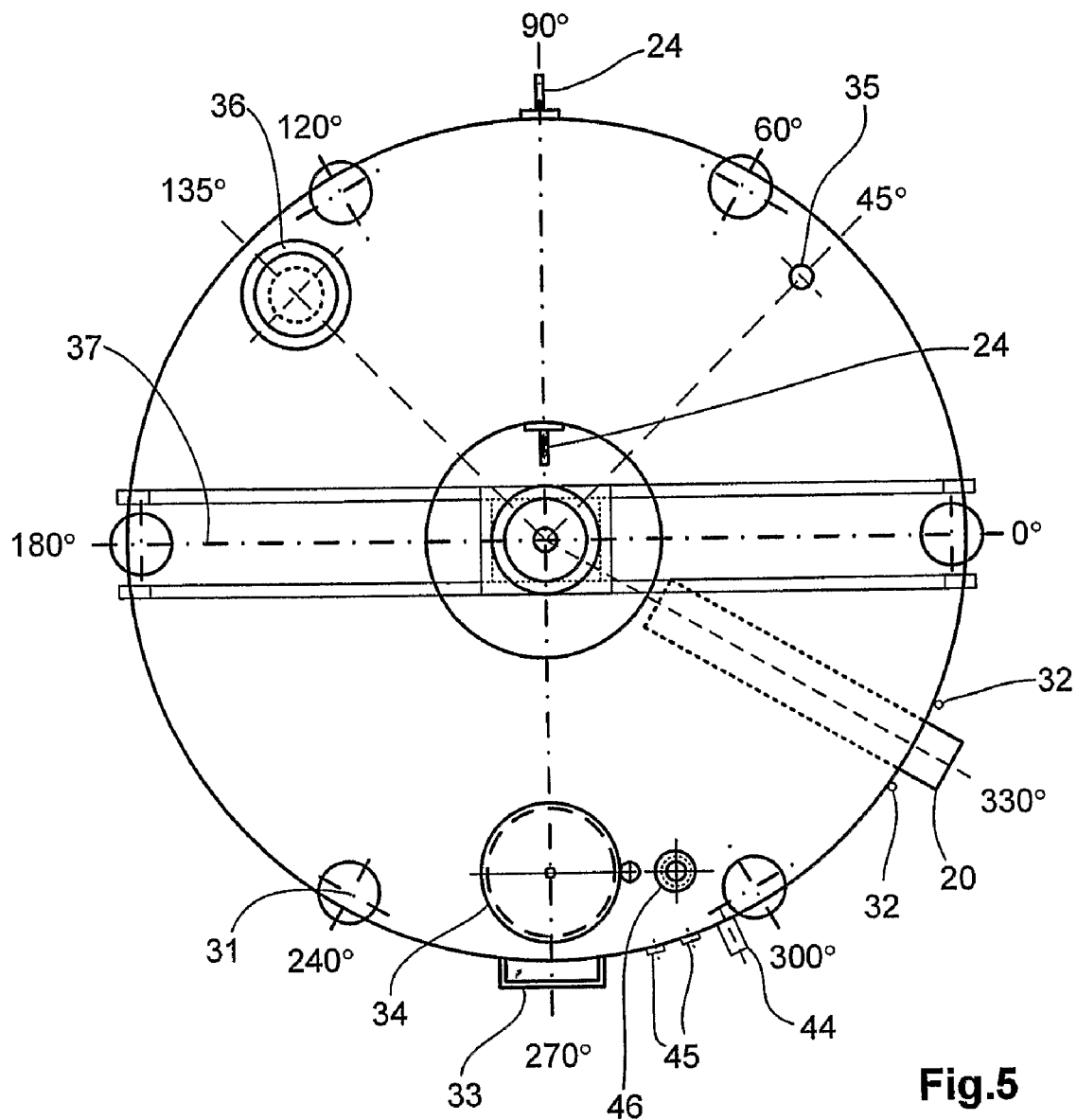
FIG. 5 shows an elevational view of the hydrolysis tank in FIG. 2.

The stirring mechanism consists of a motor 38 driving a rotating shaft 39 connected to other rotating shafts 40, which in turn are connected to a stirring rod 41 with stirring blades 42 attached. The stirring blades 42 are mounted so that, during operation, they will sweep close to the bottom of the tank. As shown in FIG. 5, this preferred embodiment of the invention comprise three stirring blades, but a higher number of blades may, of course, be used. A supporting beam 43 may also be arranged between the stirring rod 41 and the internal cylinder 28 to provide the stirring mechanism with added support.

During a normal working cycle, the tank is initially filled with hot water and raw materials through the inlet 35. These are mixed by rotation of the stirring mechanism, and at the same time, the screws 21 at the bottom of the tank are rotated, so that the treads move towards the center of the tank (which is the direction opposite to the direction of rotation applied when emptying the tank) to constantly move raw material towards the center of the tank. These screws are of a novel kind, and have previously not been used in hydrolysis tanks. Thus, a very effective mixing of water and raw materials is obtained, and with a homogeneous distribution of temperature through-out the contents of the tank.

During mixing, temperature is regulated by letting steam into the heating jackets. While still stirring, after water and raw materials are mixed, enzymes are added. The reaction will be immediate. When the hydrolysis is completed, the enzymes will be inactivated by letting more steam into the heating jackets, so that the temperature of the mixture will reach the level of inactivation for the enzymes. Temperature regulation in the tank is very accurate. This is achieved through a combination of large heating surfaces and effective stirring.

Figure 3:
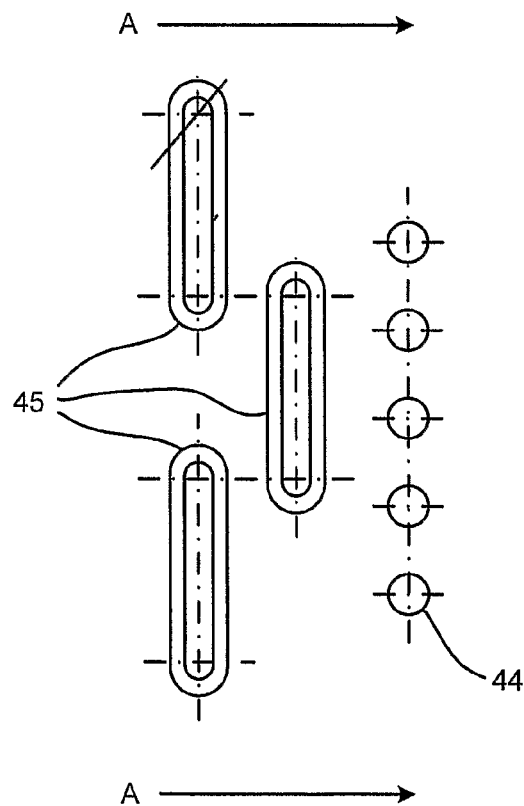
FIG. 3 shows the section A-A in the side view of FIG. 2.
Figure 2:
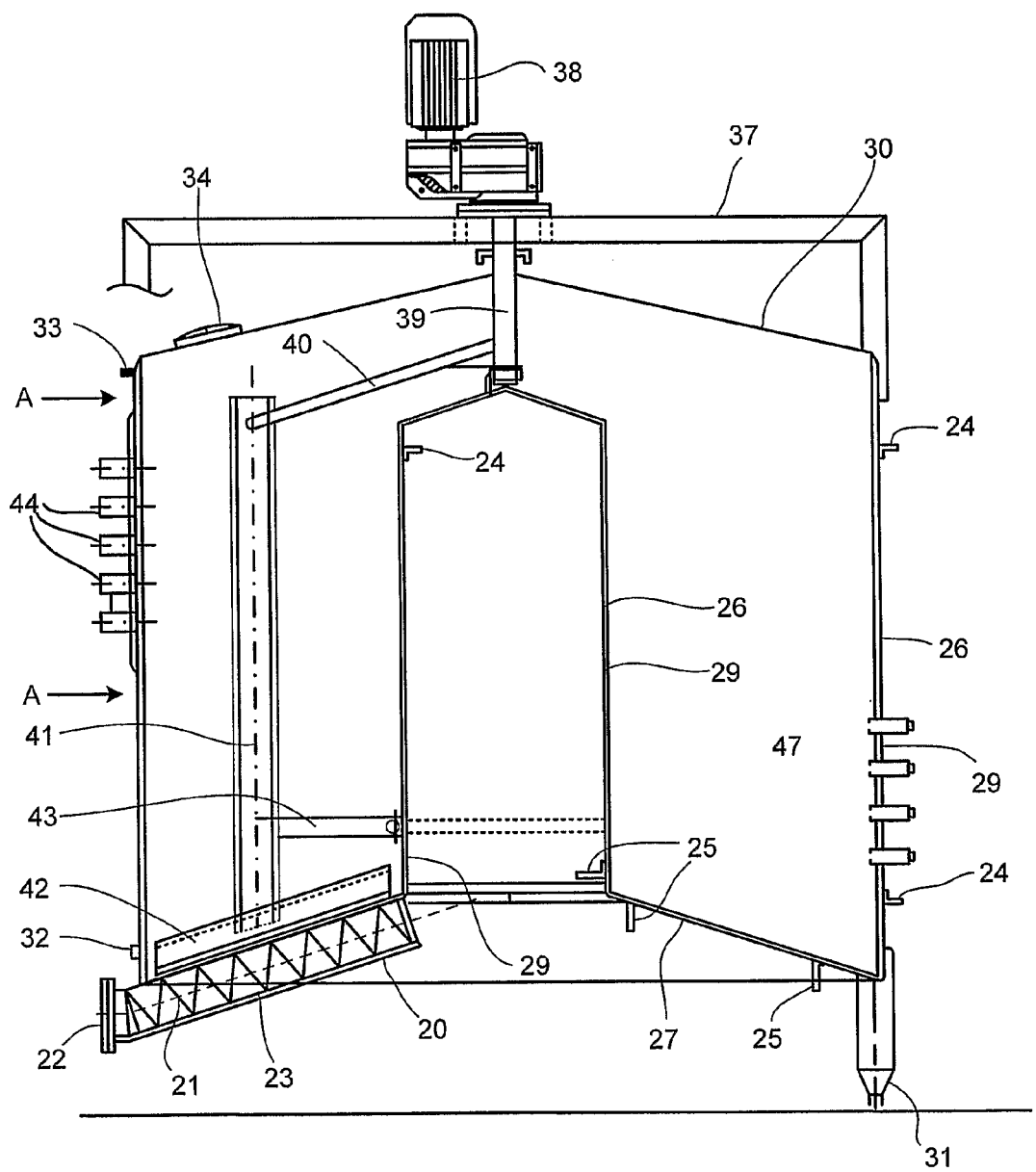
FIG. 2 shows a side view of a hydrolysis tank according to a preferred embodiment of the invention.
Figure 4:
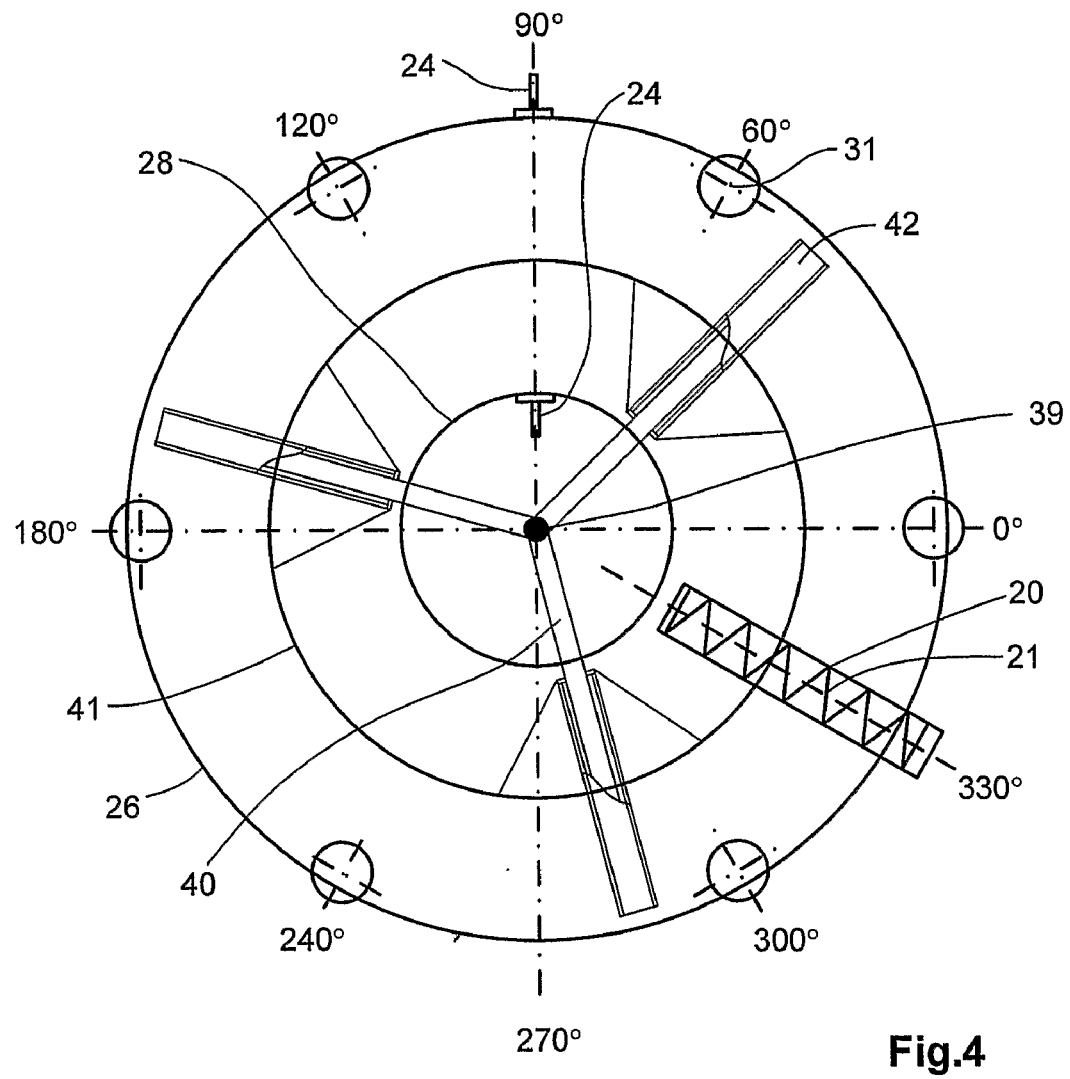
FIG. 4 shows a top view of the hydrolysis tank in FIG. 2.

Having reached the level of inactivation for the enzymes, stirring is terminated and, due to gravity, the layers start forming. Outlets for oil drainage 44, are mounted at different heights, so that drainage from a suitable outlet point can be achieved. To keep the hydrolyzat from whirling up, an outlet above the area between the oil layer and the hydrolyzat will be used initially, and then at the end of the drainage, the lowermost outlet in the oil layer will be used. Depending on the kind of raw material being processed, the amount of oil will vary, and outlets at different heights will be desirable, to be able to drain as much oil as possible, without, at the same time, draining fluid from the hydrolyzat layer. FIG. 3 shows these outlets as viewed in section A-A in FIG. 2. FIG. 3 also shows windows 45, which will provide for viewing into the tank. One may thus inspect the oil level, and determine which outlet 44 will be the most suitable. A window with a light source 46 mounted through the ceiling of the tank may also be employed to inspect the interior of the tank.

When the drainage of oil is completed, the hydrolyzat will be drained. If the fluid level in the tank is very high, this will be done initially by using the lower oil outlets 44. Regular outlets 47 for the hydrolyzat will then be used. It will be desirable to employ outlets as high on the tank as possible, and not first using the outlets near the bottom of the tank, since this will disturb the separation of the layers, causing remains of bone form the bottom layer to whirl up into the hydrolyzat.

This applies for the drainage of oil as well. If the level of hydrolyzat drops below the lowermost outlet 47, due to a small amount of remains of bone, the hydrolyzat may be pumped through the screws 21. The larger bone parts will then act as a strainer, preventing the smaller bone parts from following the hydrolyzat. Finally, the bone layer will be removed through the screws 21.

The direction of rotation for the screws 21 will then be the opposite to the direction applied during stirring. The screws 21 will now push the remains of bone out of the tank. During removal of this layer, the stirring mechanism will be operating, so that the substance will fall into the openings where the screws are situated. This is rational, since the layer is very hard to pump.

Conventional hydrolysis systems also apply screws, but for a totally different purpose. The screws are driven continuously in the same direction, to obtain a continuous movement of the hydrolyzat. The hydrolyzat is thus passes through different temperature zones, the intention being that it will pass through the system at an even rate, spending the desired amount of time in the different temperature zones. However, in practice it does not work quite that way; there being a lot of free movement of fluid inside of the screws, thus the hydrolyzat will not pass through the system at an even rate, and it will not spend the optimal amount of time at the different temperature zones.

While this tank was designed for use in an enzymatic hydrolysis process, the application of the tank will not be limited to enzymatic hydrolysis. The tank is also well suited for hydrolysis through ensilage. As in the case of enzymatic hydrolysis, the same raw materials will be used, but instead of water and enzymes, water and acid will be added, possibly with the addition of other chemicals. The hydrolysis process will then work at high temperatures, and as in the case of enzymatic hydrolysis, an even temperature and thorough mixing are important. By using this tank, one will obtain a high temperature that can be kept even, through-out the separation stage, as opposed to the systems currently used, where large temperature fluctuations occur, due to the employment of a preheater for heating of the raw materials prior to ensilage.

The Clearing Sump

The collagen contained in the hydrolysis layer will be separated from the remaining water soluble proteins by precipitation in the clearing sump. This process is novel, and the clearing sump, to carry out the process, is newly developed. The concept is simple: If the hydrolyzat is given respite at a temperature that is sufficiently low for the collagen to separate and set in a bottom layer, the rest of the hydrolyzat, which will remain liquid after setting of the collagen, may be drained and thus separated from the collagen. The collagen may then undergo a reheating, to again become liquid, and subsequently drained.

There are in particular two factors that are essential for the separation of the collagen to succeed. The clearing sump is specifically designed to this end. Firstly, it is important, for the collagen to set and that it should rest completely undisturbed. Stirring, or other forms of agitation, should therefore not be applied to obtain the necessary distribution of temperature in the hydrolyzat. It is essential that the temperature remains even throughout the contents of the sump. If the temperature is uneven, collagen at different parts of the sump will set at different points in time. Some of the remaining hydrolyzat may even freeze before all of the collagen is set, so that it cannot be drained. Secondly, the time frame is important, for the process not to come to a stop, but most of all because microorganisms easily could flourish and destroy the product. For the process to be acceptable for the preparing of food for humans, providing for swift cooling and heating possibilities is thus very important.

Figure 6:
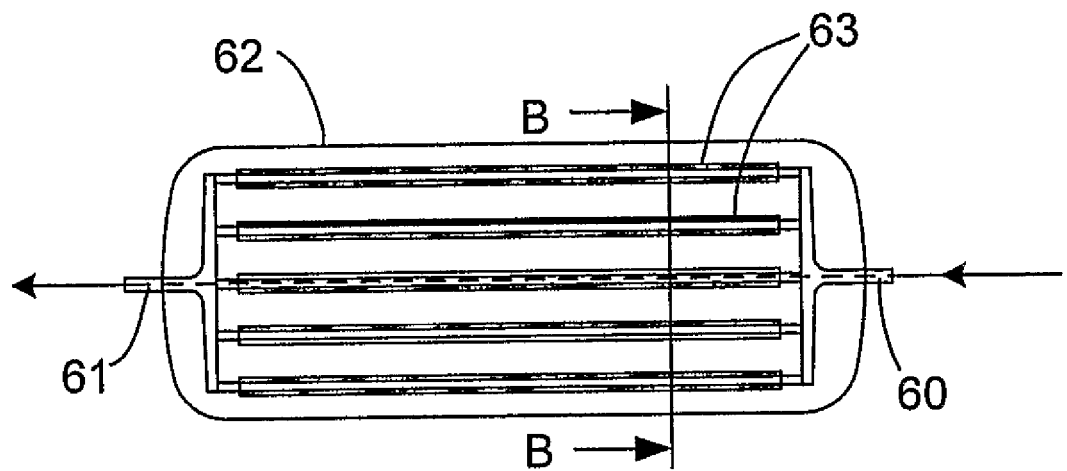
FIG. 6 shows a top view of a clearing sump according to a preferred embodiment of the invention.
Figure 7:
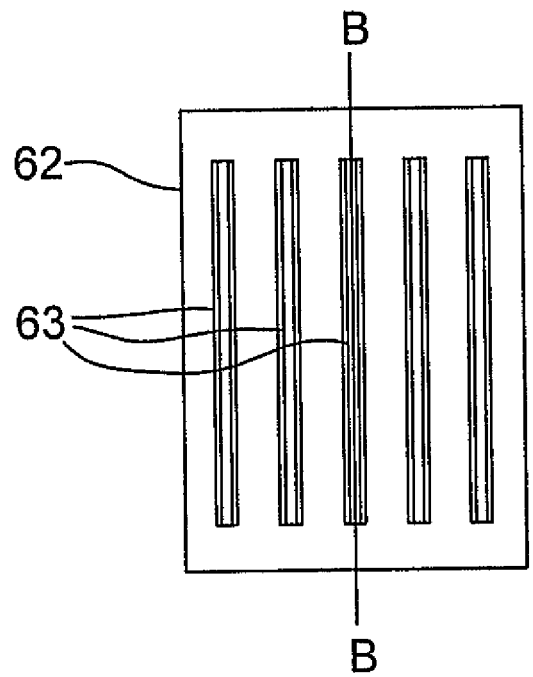
FIG. 7 shows the section B-B of the clearing sump in FIG. 6.

Accordingly, the clearing sump is designed to include a significant number of heating/cooling surfaces, so that the contents of the sump may be cooled without agitation. Surfaces here means surfaces that are in contact with the hydrolyzat. FIG. 6 shows a top view of the clearing sump. Water or steam at different temperatures is used to cool or heat the contents of the sump. The water will enter through the inlet 60, and exit through the outlet 61. The water will cool/heat both a jacket at the exterior of the clearing sump 62, as well as water filled cooling/heating surfaces 63 at the interior of the sump. It will be these cooling/heating surfaces at the interior of the sump, that provide for the possibility of swiftly achieving cooling or heating of the hydrolyzat as well as the collagen. FIG. 7 shows a side view of the clearing sump, clearly illustrating that the cooling/heating surfaces 63 are large surfaces extending almost the entire height of the sump.

The cooling/heating surfaces 63 are hollow plates, so that water is allowed to flow through them, preferably provided with grooves or ribs to increase the surface area even more. Thus, a large surface area is obtained, for the heat exchange between the water flowing through the heating surfaces and the hydrolyzat in the sump. The number of cooling/heating surfaces may of course vary, as may also the dimensions of these and the clearing sump itself. It is essential that the ratio of the surface area of the cooling/heating surfaces to the volume of the hydrolyzat is large. The cooling/heating surfaces may have wave form to increase the surface area. It is necessary for the cooling/heating surfaces to be arranged vertically; if they were to be arranged horizontally, collagen might be caught on top of them, instead of falling to the bottom of the sump. By applying only heating jackets at the sides and bottom of the sump, and not using cooling/heating surfaces at the interior of the sump, the cooling process will run too slowly. Resorting to colder water, to accelerate the cooling process, would not work, since the water will of course freeze. But even if one were to apply some other type of liquid or gas, or if one were to run the water faster through the jackets, one would still get an uneven distribution of temperature, so that the contents of the sump close to the walls would freeze, before the contents in the middle of the sump would be able to set. Letting the cooling go on for a longer period of time, very often leads to problems in relation to microbial contamination, since this allows the contents of the sump too remain to long at temperatures that are favourable for this kind of microbial growth. Using the clearing sump according to the invention, the clearing process will normally be done in under two hours, often about 1½ hours.

In the same way as for the hydrolysis tank, the size of clearing sump may of course vary as well.

When the hydrolyzat is initially loaded into the clearing sump, it may be at a high temperature. The temperature will vary, depending on the activation temperature for the enzymes used during the hydrolysis, or the time span between removal of the hydrolyzat from the hydrolysis tank and transfer to the clearing sump, etc., but normally it will be high, perhaps 80-100° C. To obtain a quick cooling of the hydrolyzat, cold water is circulated through the cooling jacket and the cooling plates, and when the temperature is sufficiently low, the collagen will change from liquid state to a gelantinous substance, and sink to the bottom of the sump. When a clearly defined surface separating the collagen from the liquid containing the remaining water soluble proteins is established, the liquid is drained.

Like the hydrolysis tank, the clearing sump also has only one inlet and several outlets. The outlets are, like the outlets for oil and hydrolyzat in the hydrolysis tank, arranged at different heights of the sump. When the liquid containing the remaining water soluble proteins is to be drained, outlets situated above the collagen are used when draining the collagen, an outlet close to, or at the bottom of the sump, is used so that the sump can be emptied completely.

When the liquid containing the remaining water soluble proteins has been removed, the collagen may be reheated through the circulation of hot water through the heating jacket and the cooling/heating surfaces. The collagen will thus return to the liquid state, and may be pumped out of the sump for further treatment.

The invention claimed is:

1. A method for the enzymatic hydrolysis of raw materials containing collagen and proteins and the separation of collagen from water soluble proteins, comprising the steps of:
   (1) enzymatically hydrolyzing the raw materials containing proteins and collagen in water to produce three layers comprising:
   (a) a top layer containing fat,
   (b) a mid-layer comprising water soluble constituents, water soluble proteins and denatured collagen, and
   (c) a non-soluble bottom layer comprising bones and non-soluble proteins;
   (2) separating said layers (a), (b) and (c); and
   (3) further separating said layer (b), comprising cooling said layer (b), without agitation, until said layer (b) reaches a temperature sufficient, and for a time period sufficient, for forming two layers, including a bottom layer (d) containing at least partially set collagen, and a liquid top layer (e) containing remaining water soluble proteins;
   (4) removing said layer (e); and
   (5) heating said layer (d) until said layer (d) becomes liquid.

2. The method according to claim 1, wherein the enzymatic hydrolysis occurs in a tank, wherein during the separating of said layers (a), (b) and (c), the non-soluble bottom layer (c) is removed through an outlet by rotating a transport screw located in a bottom portion of the tank in a direction to remove the non-soluble layer.

3. The method according to claim 2, wherein the transport screw is located in a recess in the bottom portion of the tank and is connected to the bottom of the tank by a slot, and wherein the raw materials in the tank undergo stirring, and the non-soluble bottom layer (c), during the stirring, falls into the recess, to a working area of the transport screw, and is removed through the outlet.

4. The method according to claim 2, additionally comprising reversing direction of the rotation of the transport screw.

5. The method according to claim 1, wherein during said enzymatic hydrolysis, the raw materials containing collagen and proteins are stirred in a tank with a mechanical stirring device, and a transport screw disposed in a bottom portion of the tank is rotated in a direction causing substances that have fallen down to a working area of the screw back to be led back to a central portion of the tank.

6. The method according to claim 1, wherein the further separating step (3) comprises directing said layer (b) to a receptacle containing a heat exchanger in which heat exchange fluid is circulated, the heat exchanger comprising a heat exchange jacket surrounding the receptacle and vertical heat exchange surfaces within the receptacle.

7. The method according to claim 1, wherein the raw materials containing collagen and proteins are from at least one of fish, shellfish, animals or birds.

8. The method according to claim 1, wherein the raw materials containing collagen and proteins comprise by-products from at least one of the fishing industry and the slaughterhouse industry.

9. The method according to claim 1, wherein said cooling of layer (b) takes place, without agitation, to a temperature of 10-25° C. for fish raw materials or 30-45° C. for bird raw materials.

10. The method according to claim 1, wherein said enzymatic hydrolysis comprises heating a mixture of said water and said raw materials containing collagen and proteins adding enzymes to the heated mixture, and stirring the heated mixture containing collagen and proteins to which enzymes have been added for a time period.

11. A hydrolysis tank comprising an inlet for supply of raw materials and at least one outlet for products in a bottom portion of the tank, a turnable stirring mechanism disposed for stirring raw material contained within the tank, a device for heat exchange constructed and arranged for adjustment of temperature of raw materials contained within the tank, and at least one reversibly rotatable transport screw having a working area, arranged in a bottom portion of the tank leading to the at least one outlet.

12. The hydrolysis tank according to claim 11, wherein the transport screw is rotatable in a first direction for removal of a non-soluble bottom layer of material in the tank through the at least one outlet.

13. The hydrolysis tank according to claim 12, wherein the transport screw is arranged in a recess in the bottom portion of the tank and connected to a bottom of the tank by way of a slot,
    enabling thereby the non-soluble bottom layer of material in the tank, under stirring, to fall into the recess, to the working area of the screw, and be removed from the tank through the at least one outlet.

14. The hydrolysis tank according to claim 11, wherein the transport screw is reversible to rotate in a second direction, to lead substances that have fallen down to the working area of the screw back into a central area of the tank.

15. The hydrolysis tank according to claim 11, wherein the stirring device comprises a blade stirrer, having at least one blade arranged to sweep the bottom portion of the tank.

16. The hydrolysis tank according to claim 11, additionally comprising in communication with one said outlet thereof a clearing sump comprising a receptacle containing a heat exchanger in which heat exchange fluid is circulated, the heat exchanger comprising both a heat exchange jacket surrounding the receptacle and vertical heat exchange surfaces within the receptacle.

* * * * *